US012680959B2

(12) United States Patent
Al-Humam et al.

(10) Patent No.: US 12,680,959 B2
(45) Date of Patent: Jul. 14, 2026

(54) SIDEROPHORE-BASED BIOSENSORS FOR IRON DETECTION

(71) Applicant: Saudi Arabian Oil Company, Dhahran (SA)

(72) Inventors: Abdulmohsen A. Al-Humam, Dammam (SA); Nora K. Al-Sudairi, Dhahran (SA); Manar A. AlAhmari, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 712 days.

(21) Appl. No.: 18/149,438

(22) Filed: Jan. 3, 2023

(65) Prior Publication Data

US 2024/0219303 A1     Jul. 4, 2024

(51) Int. Cl.
*G01N 21/64*        (2006.01)
*G01N 33/18*        (2006.01)

(52) U.S. Cl.
CPC ....... *G01N 21/643* (2013.01); *G01N 33/1813* (2013.01)

(58) Field of Classification Search
CPC ...... G01N 21/64; G01N 21/643; G01N 33/18; G01N 33/1813; G01N 33/84; G01N 33/20; E21B 47/006; E21B 43/20; C12Q 1/64
USPC ..... 436/40, 60, 73, 84, 164, 172; 422/82.05, 422/82.08; 435/7.32, 29, 253.3
See application file for complete search history.

(56) References Cited

U.S. PATENT DOCUMENTS

| | | | | |
|---|---|---|---|---|
| 2012/0325740 | A1 | 12/2012 | Kruglick | |
| 2016/0319322 | A1* | 11/2016 | Miller | .............. G01N 33/54387 |
| 2025/0187058 | A1* | 6/2025 | Milovanovic | .......... A61K 45/06 |

FOREIGN PATENT DOCUMENTS

| | | |
|---|---|---|
| CN | 115544754 | 12/2022 |
| CN | 115544754 A | * 12/2022 |

OTHER PUBLICATIONS

Barrero et al. Analyst, vol. 120, Feb. 1995, pp. 431-435.*
Kumar et al. Jounral of Biology and Chemistry, vol. 298(3), article 101651, 2022, pp. 1-16.*
Abergel et al., "Anthrax pathogen evades the mammalian immune system through stealth siderophore production," Proceedings of the National Academy of Sciences of the United States of America, Dec. 2006, 103(49): 18499-18503, 5 pages.

Cendrowski et al., "Bacillus anthracis requires siderophore biosynthesis for growth in macrophages and mouse virulence," Molecular Microbiology, Jan. 2004, 51(2):407-417, 11 pages.
Challis, "A widely distributed bacterial pathway for siderophore biosynthesis independent of nonribosomal peptide synthetases," ChemBioChem, Apr. 2005, 6(4):601-611, 11 pages.
Crosa et al., "Iron Transport in Bacteria," ASM Press, 2004, 17 pages.
Hider et al., "Chemistry and biology of siderophores," Natural Product Reports, May 2010, 27(5):637-57, 21 pages.
Hossain et al., "Circular Dichroism, Crystal Structure, and Absolute Configuration of the Siderophore Ferric N,N',N"-Triacetylfusarinine, $FeC_{39}H_{57}N_6O_{15}$," Journal of the American Chemical Society, Aug. 1980, 102(18):5766-5773, 8 pages.
Johnstone et al., "Beyond iron: non-classical biological functions of bacterial siderophores," Dalton Transactions, Apr. 2015, 44(14):6320-6339, 20 pages.
Kraemer, "Iron oxide dissolution and solubility in the presence of siderophores," Aquatic Sciences, Mar. 2004, 66(1):3-18, 17 pages.
Miethke et al., "Siderophore-based iron acquisition and pathogen control," Microbiology and Molecular Biology Reviews, Sep. 2007, 71(3):413-451, 39 pages.
Miller et al., "Microbial iron chelators as drug delivery agents: the rational design and synthesis of siderophore-drug conjugates," Accounts of Chemical Research, Mar. 1993, 26(5):241-249, 9 pages.
Neilands, "Siderophores: structure and function of microbial iron transport compounds," The Journal of Biological Chemistry, Nov. 1995, 270(45):26723-26726, 4 pages.
Raymond et al., "Enterobactin: an archetype for microbial iron transport," Proceedings of the National Academy of Sciences of the United States of America, Apr. 2003, 100(7):3584-3588, 5 pages.
Yoder et al., "Iron specificity of a biosensor based on fluorescent pyoverdin immobilized in sol-gel glass," Journal of Biological Engineering, Dec. 2011, 5(4):1-12, 12 pages.
Hu et al., "Whole-Cell Biosensing by Siderophore-Based Molecular Recognition and Localized Surface Plasmon Resonance," Analytical Methods, Dec. 2018, 11:296-302, 7 pages.
Lam et al., "Fluorescence-Based Siderophore Biosensor for the Determination of Bioavailable Iron in Oceanic Waters," Analytical Chemistry, Jul. 2006, 78(14):5040-5045, 6 pages.
Nosrati et al., "Siderophore-based biosensors and nanosensors; new approach on the development of diagnostic systems," Biosensors and Bioelectronics, May 2018, 29 pages.
Pulido-Tofino et al., "A flow-through fluorescent sensor to determine Fe (III) and total inorganic iron," Talanta, Mar. 2000, 51(3):537-545, 9 pages.
Sharma et al., "Optical features of the fluorophore azotobactin: Applications for iron sensing in biological fluids," Engineering in Life Sciences, Aug. 2010, 10(4):304-310, 7 pages.
International Search Report and Written Opinion in International Appln No. PCT/US2024/010148, dated May 3, 2024, 17 pages.

* cited by examiner

*Primary Examiner* — Maureen Wallenhorst
(74) *Attorney, Agent, or Firm* — Fish & Richardson P.C.

(57)     ABSTRACT

This disclosure relates to methods of detecting iron in a water injection system, such as a water injection system used in the oil and gas industry, using an optical siderophore-based biosensor. This disclosure also relates to methods of detecting corrosion using an optical siderophore-based biosensor.

22 Claims, No Drawings

SIDEROPHORE-BASED BIOSENSORS FOR IRON DETECTION

TECHNICAL FIELD

This document relates to biosensors that are based on siderophores, such as siderophore-based optical biosensors. The biosensors can be used in the oil and gas industry, such as in a water injection system, to detect the presence of iron, and thereby corrosion.

BACKGROUND

Corrosion is a process by which materials are degraded or deteriorated due to reaction with their environment. Corrosion of metals occurs via a redox reaction that turns the surface of metals from their manufactured state into their natural and original form. Most metals, when they come in contact with certain environmental factors, such as temperature, humidity, salinity, and dissolved oxygen concentration, become susceptible to oxidative reactions that are responsible for the loss of their current properties, as most metals are more stable as oxides. Carbon steel is an example of a metal important to a broad spectrum of industries and machineries, and the inhibition of steel corrosion has trigged significant academic and industrial concerns.

Various metal binding ligands and techniques have been proposed for the determination of iron. While current techniques for measuring iron can be very accurate, they are often very expensive, may involve large pieces of equipment, and can involve time-consuming procedures.

Many industrial processes, such as in the oil and gas industry, could benefit from an economical, rapid, and sensitive iron biosensor. Thus, there is a need for a method that can be used to detect and identify iron and, for example, corrosion in early stages, such as in the oil and gas industry.

SUMMARY

Provided in the present disclosure is a method for detecting the presence or concentration of iron in a water injection system. In some embodiments, the method includes:

contacting a biosensor with a sample of water from a water injection system, where the biosensor includes an iron chelator produced by a bacteria, where the iron chelator transduces a detectable signal; and a permeable matrix entrapping or encapsulating the iron chelator;

measuring a signal from the biosensor, where a signal transduced by the iron chelator when the iron chelator is bound to iron differs from a signal transduced by the iron chelator when the iron chelator is not bound to iron; and comparing the signal to an iron control value, where a difference in signal indicates the presence of iron in the sample.

In some embodiments of the method, the bacteria is selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii,* and *Paracoccus denitrificans*. In some embodiments, the bacteria is *Pseudomonas aeruginosa*. In some embodiments, the bacteria is *Azotobacter vinelandii*. In some embodiments, the bacteria is *Paracoccus denitrificans*. In some embodiments, the bacteria is *Acinetobacter baumannii*.

In some embodiments of the method, the iron chelator is a fluorescent siderophore. In some embodiments, the fluorescent siderophore is selected from the group consisting of pyoverdin, azotobactin, parabactin, and acinetobactin. In some embodiments, the fluorescent siderophore is pyoverdin. In some embodiments, the fluorescent siderophore is azotobactin. In some embodiments, the fluorescent siderophore is parabactin. In some embodiments, the fluorescent siderophore is acinetobactin. In some embodiments, the iron chelator chelates ferric iron (Fe(III)).

In some embodiments of the method, the detectable signal is a fluorescent signal.

In some embodiments of the method, the permeable matrix is a sol-gel. In some embodiments, the sol-gel is a sol-gel glass. In some embodiments, the permeable matrix is a sol-gel thin film on a quartz substrate.

In some embodiments of the method, the water injection system is part of an oil and gas pipeline, oil and gas storage tank, or oil and gas vessel.

Also provided in the present disclosure is a method for detecting corrosion in a water injection system. In some embodiments, the method includes:

contacting a biosensor with a sample of water from a water injection system, where the biosensor includes an iron chelator produced by a bacteria, where the iron chelator transduces a detectable signal; and a permeable matrix entrapping or encapsulating the iron chelator;

measuring a signal from the biosensor, where a signal transduced by the iron chelator when the iron chelator is bound to iron differs from a signal transduced by the iron chelator when the iron chelator is not bound to iron; and comparing the signal to an iron control value, where a difference in signal indicates the presence of iron in the sample.

In some embodiments of the method, the bacteria is selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii,* and *Paracoccus denitrificans*.

In some embodiments of the method, the iron chelator is a fluorescent siderophore selected from the group consisting of pyoverdin, azotobactin, acinetobactin, and parabactin. In some embodiments, the iron chelator chelates ferric iron (Fe(III)).

In some embodiments of the method, the permeable matrix is a sol-gel. In some embodiments, the sol-gel is a sol-gel glass. In some embodiments, the permeable matrix is a sol-gel thin film on a quartz substrate.

In some embodiments of the method, the water injection system is part of an oil and gas pipeline, oil and gas storage tank, or oil and gas vessel.

Also provided in the present disclosure is a method for detecting the presence or concentration of iron in a water injection system. In some embodiments, the method includes:

contacting a biosensor with a sample of water from a water injection system, where the biosensor includes a fluorescent siderophore produced by a bacteria selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii,* and *Paracoccus denitrificans*, where the fluorescent siderophore is an iron chelator; and a permeable matrix entrapping or encapsulating the fluorescent sidero-phore;

measuring a signal from the biosensor, where a signal transduced by the fluorescent siderophore when the fluorescent siderophore is bound to iron differs from a signal transduced by the fluorescent siderophore when the fluorescent siderophore is not bound to iron; and comparing the signal to an iron control value, where a difference in signal indicates the presence of iron in the sample.

In some embodiments of the method, the fluorescent siderophore is selected from the group consisting of pyover-din, azotobactin, acinetobactin, and parabactin.

In some embodiments of the method, the iron chelator chelates ferric iron (Fe(III)).

In some embodiments of the method, the permeable matrix is a sol-gel. In some embodiments, the sol-gel is a sol-gel glass. In some embodiments, the permeable matrix is a sol-gel thin film on a quartz substrate.

In some embodiments of the method, the presence of iron indicates corrosion.

DETAILED DESCRIPTION

Water injection (or water flooding) is a secondary hydro-carbon recovery technique where water, such as produced water, treated or demineralized water, or freshwater, is injected into a well's formation under high pressure and temperature conditions in order to recover more of the oil initially in place (OIIP). The corrosion of metal used in water injection systems used in the oil and gas industry can pose serious problems and early detection is desirable. Provided in the present disclosure is a siderophore-based biosensor that can be used in the oil and gas industry, for example, for detecting the presence or concentration of iron in a water injection system. Also provided are methods of using the biosensor to detect corrosion, such as in a water injection system.

The methods of the present disclosure involve the use of optical biosensors to detect the presence of iron in a sample, such as a water sample. A biosensor is a biomolecule coupled to an electrical device such as a transducer, ampli-fier, or noise filter in order to increase the signal-to-noise ratio that allows detection of various types of responses through specifically engineered systems. The biosensors of the present disclosure are able to detect quantities of, includ-ing very small quantities of, or changes in, a biochemical or chemical substance, in which an intermolecular binding event is registered and translated into data. The biosensors of the present disclosure can be used to detect the presence of iron, and in particular, ferric iron (Fe(III)) in a sample. In some embodiments, the biosensors of the present disclosure selectively bind to Fe(III) over other forms of iron. The presently disclosed biosensors combine the molecular rec-ognition properties of biological macromolecules, such as a binding member of a specific binding pair, with a fluoro-phore capable of transducing a detectable signal, for example, a detectable change in one or more fluorescent properties, upon binding with a target molecule, such as iron. The term "transduce a detectable signal" refers to the ability to recognize a change in a property of a reporter group, for example, a fluorophore, in a manner that enables the detection of iron-iron chelator binding. Thus, a biosensor can translate a binding event into a directly measurable fluorescent property. Such changes in one or more fluores-cence properties include, but are not limited to, an increase or decrease in fluorescence intensity, a shift in excitation or emission maxima, a change in the shape of the excitation or emission band profiles, a change in fluorescence lifetime, a change in anisotropy, a change in polarization, and combi-nations thereof. Further, the producing of a detectable signal can be reversible or non-reversible. The signal-producing event can include continuous, programmed, and episodic means, including one-time or reusable applications. The reversible signal-producing event can be instantaneous or can be time-dependent, so long as a correlation with the presence or concentration of target molecule (e.g., iron) is established.

The optical biosensors of the present disclosure are made up of an iron chelator capable of transducing a detectable signal, such as a fluorescent signal, and a permeable matrix entrapping or encapsulating the iron chelator. In some embodiments, the iron chelator is produced by a bacteria. In some embodiments, the bacteria is a fluorescent bacteria. In some embodiments, the bacteria is a fluorescent bacteria selected from the genus *Pseudomonas, Azotobacter, Acine-tobacter*, or *Paracoccus*. In some embodiments, the fluo-rescent bacteria is selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter bauman-nii*, and *Paracoccus denitrificans*. In some embodiments, the bacteria is *Pseudomonas aeruginosa*. In some embodiments, the bacteria is *Azotobacter vinelandii*. In some embodi-ments, the bacteria is *Acinetobacter baumannii*. In some embodiments, the bacteria is *Paracoccus denitrificans*.

In some embodiments, the iron chelator is a siderophore. The term "siderophore," as used in the present disclosure, refers to a molecule that binds and transports iron. A siderophore can be a natural siderophore secreted by micro-organisms such as bacteria or fungi or can be a synthetic siderophore. In some embodiments, the siderophores of the present disclosure are synthesized or produced by a bacteria. In some embodiments, the iron chelator is a siderophore produced by a fluorescent bacteria such as described in the present disclosure. In some embodiments, the siderophore is a synthetic fluorescent siderophore. Siderophores are gen-erally low molecular weight compounds (for example, less than about 2,000 MW) and can exhibit either or both cellular uptake and iron storage functions.

The siderophores of the present disclosure form a strong complex with Fe(III) and have a weak or negligible affinity for Fe(II). In some embodiments, the resulting Fe(III) com-plexes have very high stability constants (approximately K=1032). Thus, the biosensors of the present disclosure containing the siderophores are sensitive and highly selec-tive. Using the biosensors containing the siderophores with exceptional Fe(III)-binding constants allows for the molecu-lar recognition element of the sensor to be applied in the determination of iron bioavailability in a sample, such as a water sample. In some embodiments, the water sample is from a water injection system. Exemplary water injection systems include those used in the oil and gas industry in, for example, pipelines, storage tank, vessels, etc. In some embodiments, the concentration of iron present in a water injection system is determined by using a siderophore as an optical biosensor.

In some embodiments, the iron chelator is a fluorescent siderophore produced by a bacteria from the genus *Pseudomonas, Azotobacter, Acinetobacter*, or *Paracoccus*. In some embodiments, the iron chelator is a fluorescent siderophore produced by a fluorescent bacteria selected from the group consisting of *Pseudomonas aeruginosa*,

*Pseudomonas oryzihabitans, Pseudomonas stutzeri, Pseudomonas putida, Pseudomonas fluorescens, Azotobacter vinelandii, Acinetobacter baumannii,* and *Paracoccus denitrificans.* In some embodiments, the fluorescent siderophore is produced by *Pseudomonas aeruginosa.* In some embodiments, the fluorescent siderophore is pyoverdin produced by *Pseudomonas aeruginosa.* In some embodiments, the fluorescent siderophore is produced by *Azotobacter vinelandii.* In some embodiments, the fluorescent siderophore is azotobactin produced by *Azotobacter vinelandii.* In some embodiments, the fluorescent siderophore is produced by *Acinetobacter baumannii.* In some embodiments, the fluorescent siderophore is produced by *Paracoccus denitrificans.* In some embodiments, the fluorescent siderophore is parabactin produced by *Paracoccus denitrificans.*

In some embodiments, the siderophore is entrapped or encapsulated in a permeable matrix. In some embodiments, the permeable matrix is a sol-gel matrix. Examples of sol-gel matrixes that can be included in the biosensors of the present disclosure include materials prepared by known sol-gel methods and can include inorganic material, organic material, or mixed organic/inorganic material. The materials used to produce the sol-gel can include, but are not limited to, aluminates, aluminosilicates, and titanates. In some embodiments, these materials are augmented with organically modified silicates (Ormosils) and functionalized siloxanes, in order to, for example, impart and manipulate hydrophilicity and hydrophobicity, ionic charge, or to make any other covalent modification. In some embodiments, the sol-gel includes organically modified silicates. In some embodiments, the sol-gel is a sol-gel glass. In some embodiments, the permeable matrix is a sol-gel thin film on a quartz substrate.

In some embodiments, the permeable matrix contains modified sol-gels. Modified sol-gels include at least partially cured (or gelled) preparations containing permeable metal oxide glass structures in addition to the sol-gel precursor materials, such as one or more organic components which hydrolytically condense along with the sol-gel precursor. Suitable organic materials include, but are not limited to, polyols such as glycerol, ethylene glycol, propylene glycol, and polyethylene glycol.

In some embodiments, the sol-gel matrix is optically transparent, making it useful as a chemical or biochemical sensor that relies on optical transduction, for example, absorption or fluorescence spectroscopic methods. In some embodiments, the entrapped or immobilized siderophore remains able to undergo an analyte-induced conformational change. In some embodiments, the sol-gel entrapped siderophore does not exhibit an altered binding constant, or a binding constant that changes over relatively short time periods or under varying environmental conditions. In some embodiments, encapsulation or entrapment of the siderophore in the permeable matrix does not result in significant loss of fluorescence signal from the siderophore.

Thus, also provided are methods of using the optical siderophore-based biosensors described in the present disclosure in the oil and gas industry, such as in a water injection system, to detect the presence of iron, and thereby detect corrosion. In some embodiments, the water injection system is part of an oil and gas pipeline, oil and gas storage tank, or oil and gas vessel.

Provided in the present disclosure is a method for detecting the presence or concentration of iron in a water injection system. In some embodiments, the water injection system is part of an oil and gas pipeline, oil and gas storage tank, or oil and gas vessel. In some embodiments, the method includes contacting a biosensor of the present disclosure with a sample of water from the water injection system, measuring a signal from the biosensor, and comparing the signal to an iron control value, where a difference in signal indicates the presence of iron in the sample. In some embodiments, the presence of iron in the water sample is an indicator of corrosion. In some embodiments, the biosensor includes an iron chelator produced by a bacteria, where the iron chelator transduces a detectable signal, and a permeable matrix entrapping or encapsulating the iron chelator. In some embodiments, a signal transduced by the iron chelator when the iron chelator is bound to iron differs from a signal transduced by the iron chelator when the iron chelator is not bound to iron. In some embodiments, the iron chelator is a fluorescent siderophore. In some embodiments, the detectable signal is a fluorescent signal. In some embodiments, the iron chelator chelates ferric iron (Fe(III)). In some embodiments, the iron chelator selectively chelates Fe(III) over other forms of iron. In some embodiments, the permeable matrix is a sol-gel. In some embodiments, the sol-gel is a sol-gel glass.

Also provided in the present disclosure is a method for detecting corrosion in a water injection system. In some embodiments, the water injection system is part of an oil and gas pipeline, oil and gas storage tank, or oil and gas vessel. In some embodiments, the method includes contacting a biosensor of the present disclosure with a sample of water from the water injection system, measuring a signal from the biosensor, and comparing the signal to an iron control value, where a difference in signal indicates the presence of iron in the sample. In some embodiments, the biosensor includes an iron chelator produced by a bacteria, where the iron chelator transduces a detectable signal, and a permeable matrix entrapping or encapsulating the iron chelator. In some embodiments, a signal transduced by the iron chelator when the iron chelator is bound to iron differs from a signal transduced by the iron chelator when the iron chelator is not bound to iron. In some embodiments, the iron chelator is a fluorescent siderophore. In some embodiments, the detectable signal is a fluorescent signal. In some embodiments, the iron chelator selectively chelates Fe(III) over other forms of iron. In some embodiments, the permeable matrix is a sol-gel. In some embodiments, the sol-gel is a sol-gel glass.

In some embodiments of the methods of the present disclosure, the bacteria is selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii,* and *Paracoccus denitrificans.* In some embodiments, the bacteria is *Pseudomonas aeruginosa.* In some embodiments, the bacteria is *Azotobacter vinelandii.* In some embodiments, the bacteria is *Acinetobacter baumannii.* In some embodiments, the bacteria is *Paracoccus denitrificans.* In some embodiments, the siderophore is pyoverdin. In some embodiments, the siderophore is azotobactin. In some embodiments, the siderophore is acinetobactin. In some embodiments, the siderophore is parabactin.

Unless otherwise defined, all technical and scientific terms used in this document have the same meaning as commonly understood by one of ordinary skill in the art to which the present application belongs. Methods and materials are described in this document for use in the present application; other, suitable methods and materials known in the art can also be used. The materials, methods, and examples are illustrative only and not intended to be limiting. All publications, patent applications, patents, sequences, database entries, and other references mentioned in this document are incorporated by reference in their entirety. In case of conflict, the present specification, including definitions, will control.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, and 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about," as used in this disclosure, can allow for a degree of variability in a value or range, for example, within 10%, within 5%, or within 1% of a stated value or of a stated limit of a range.

As used in this disclosure, the terms "a," "an," and "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In the methods described in this disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

EXAMPLES

Example 1—Preparation of Biosensor

Siderophore biosynthesis occurs via two pathways: the non-ribosomal peptide synthetase (NRPS) pathway and the NRPS-independent siderophore (NIS) synthetase pathway. NIS enzymes function by adenylating a carboxylic acid substrate, typically citrate, or a derivative, followed by nucleophilic capture of an amine or alcohol and displacement of a citryl intermediate.

Bacterial Isolates

One hundred twenty specimens belonging to non-fermenter Gram-negative bacilli were collected from three hospitals in Baghdad, Iraq over three months. Nineteen clinical isolates were identified as *Acinetobacter baumannii* (*A. baumannii*), and the diagnosis was confirmed by using highly selective medium CHROMagar™ *Acinetobacter* (CHROMagar, Paris, France) and the Vitek® 2 system (bioMérieux, Inc., Durham, NC).

Antibiotic Susceptibility

*A. baumannii* isolates were tested against 11 different antibiotic discs, provided by Bioanalyse (Ankara, Turkey).

Detection of Siderophores

The isolates were cultured on M9 minimum solid medium which was prepared as follows.

Dissolving: $Na_2HPO_4$ (6 g), $KH_2PO_4$ (3 g), NaCl (0.5 g), $NH_4Cl$ (1 g), and agar agar (15 g) were dissolved in 1 L deionized water, the pH was adjusted to 7.2, autoclaved, and cooled to 45° C. To the medium, the following components were added: 20 mL of $MgSO_4$ (0.5 g/20 mL), 1 mL dipyridine (0.005 g/10 mL), 1 mL $CaCl_2$) (0.03 g/10 mL), and 10 mL glucose (2 g/10 mL). The components were sterilized by filtration using 0.22 µM Millipore filters. The medium was then supplemented with 0.1 g thiamine. The components were well-mixed and poured into disposable sterile plates. After being solidified, the plates were inoculated with tested isolates (touched by sterile wood stick) and incubated at 37°C for 24 hrs. If the isolate was siderophore-producing, the growth appeared as small, single and separated colonies on the M9 medium.

Siderophore Production

A synthetic medium with the following components per liter was prepared. The pH was adjusted to 7 and autoclaved.

| Component | Weight |
| --- | --- |
| Mannitol | 10 g |
| Sodium gluconate | 2 g |
| $K_2HPO_4$ | 0.5 g |
| $MgSO_4$ | 0.2 g |
| NaCl | 0.1 g |

Extraction of Siderophore

The bacterial suspension was centrifuged at 8000 rpm/20 min. The supernatant was acidified to pH 2 and the siderophore was immediately extracted by adding an equal volume of ethyl acetate, shaken in a 50° C. water bath to evaporate the ethyl acetate layer, then the extract was placed in an oven at 50° C. in open petri dishes to obtain the dried extract.

Example 2—Biosensor Use in the Field

A biosensor is a biomolecule coupled to an electrical device such as a transducer, amplifier, or noise filter in order to increase the signal-to-noise ratio that allows for detection of various types of responses through specifically engineered systems.

Pyoverdins are yellow-green water-soluble fluorescent siderophores characterized in that they form a strong complex with Fe(III) and have a weak or negligible affinity for Fe(II). The Fe(III) complexes have very high stability constants (approximately K=1032). These characteristics make pyoverdine a promising agent for the construction of optical biosensors. A siderophore with an exceptional Fe(III) binding constant will be used for the molecular recognition element of the sensor that will then be applied in the determination of Fe bioavailability in oceanic water or soils. Parabactin will be produced by *Paracoccus denitrificans*, and used as a biosensor by encapsulating it in sol-gel thin film on a quartz substrate.

The Fe(II) and Fe(III) specificity for the Fe biosensor pyoverdine will be optimized by immobilizing it in three formulations of porous sol-gel glass (A, B, and C), which contain various amounts of water added.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting a presence of iron in a water injection system, the method comprising:

contacting a biosensor with a sample of water from the water injection system, wherein the biosensor comprises:

an iron chelator produced by a bacteria, wherein the iron chelator transduces a detectable signal; and a permeable matrix entrapping or encapsulating the iron chelator;

measuring a signal from the biosensor, wherein a signal transduced by the iron chelator when the iron chelator is bound to iron differs from a signal transduced by the iron chelator when the iron chelator is not bound to iron; and comparing the signal to a control value, wherein a difference in signal indicates the presence of iron in the sample;

wherein the water injection system is part of an oil and gas pipeline, oil and gas storage tank, or oil and gas vessel.

2. The method of claim 1, wherein the bacteria is selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii*, and *Paracoccus denitrificans.*

3. The method of claim 2, wherein the bacteria is *Pseudomonas aeruginosa.*

4. The method of claim 2, wherein the bacteria is *Azotobacter vinelandii.*

5. The method of claim 2, wherein the bacteria is *Paracoccus denitrificans.*

6. The method of claim 2, wherein the bacteria is *Acinetobacter baumannii.*

7. The method of claim 1, wherein the iron chelator is a fluorescent siderophore.

8. The method of claim 7, wherein the fluorescent siderophore is selected from the group consisting of pyoverdin, azotobactin, parabactin, and acinetobactin.

9. The method of claim 1, wherein the detectable signal is a fluorescent signal.

10. The method of claim 1, wherein the iron chelator chelates ferric iron (Fe(III)).

11. The method of claim 1, wherein the permeable matrix is a sol-gel.

12. The method of claim 11, wherein the sol-gel is a sol-gel glass.

13. A method for detecting corrosion in a water injection system, the method comprising:

contacting a biosensor with a sample of water from the water injection system, wherein the biosensor comprises:

an iron chelator produced by a bacteria, wherein the iron chelator transduces a detectable signal; and a permeable matrix entrapping or encapsulating the iron chelator;

measuring a signal from the biosensor, wherein a signal transduced by the iron chelator when the iron chelator is bound to iron differs from a signal transduced by the iron chelator when the iron chelator is not bound to iron; and comparing the signal to a control value, wherein a difference in signal indicates the presence of iron in the sample;

wherein the water injection system is part of an oil and gas pipeline, oil and gas storage tank, or oil and gas vessel, and wherein the presence of iron in the sample indicates corrosion in the water injection system.

14. The method of claim 13, wherein the bacteria is selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii*, and *Paracoccus denitrificans.*

15. The method of claim 13, wherein the iron chelator is a fluorescent siderophore selected from the group consisting of pyoverdin, azotobactin, acinetobactin, and parabactin.

16. The method of claim 13, wherein the iron chelator chelates ferric iron (Fe(III)).

17. The method of claim 13, wherein the permeable matrix is a sol-gel.

18. A method for detecting a presence of iron in a water injection system, the method comprising:

contacting a biosensor with a sample of water from the water injection system, wherein the biosensor comprises:

a fluorescent siderophore produced by a bacteria selected from the group consisting of *Pseudomonas aeruginosa, Pseudomonas oryzihabitans, Pseudomonas stutzeri, Pseudomonas putida, Pseudomonas fluorescens, Azotobacter vinelandii, Acinetobacter baumannii*, and *Paracoccus denitrificans*, wherein the fluorescent siderophore is an iron chelator; and a permeable matrix entrapping or encapsulating the fluorescent siderophore;

measuring a signal from the biosensor, wherein a signal transduced by the fluorescent siderophore when the fluorescent siderophore is bound to iron differs from a signal transduced by the fluorescent siderophore when the fluorescent siderophore is not bound to iron; and comparing the signal to a control value, wherein a difference in signal indicates the presence of iron in the sample;

wherein the water injection system is part of an oil and gas pipeline, oil and gas storage tank, or oil and gas vessel.

19. The method of claim 18, wherein the fluorescent siderophore is selected from the group consisting of pyoverdin, azotobactin, acinetobactin, and parabactin.

20. The method of claim 18, wherein the iron chelator chelates ferric iron (Fe(III)).

21. The method of claim 18, wherein the permeable matrix is a sol-gel.

22. The method of claim 18, wherein the presence of iron indicates corrosion in the water injection system.

* * * * *